(12) United States Patent
Currier (10) Patent No.: US 10,016,305 B2
(45) Date of Patent: Jul. 10, 2018

(54) CLIP-ON EARMUFF AND KIT

(71) Applicant: Gary H. Currier, Andover, NH (US)

(72) Inventor: Gary H. Currier, Andover, NH (US)

( * ) Notice: Subject to any disclaimer, the term of this patent is extended or adjusted under 35 U.S.C. 154(b) by 372 days.

(21) Appl. No.: 14/477,422

(22) Filed: Sep. 4, 2014

(65) Prior Publication Data

US 2016/0067101 A1   Mar. 10, 2016

(51) Int. Cl.
*A42B 1/06* (2006.01)
*A61F 11/14* (2006.01)

(52) U.S. Cl.
CPC ............. *A61F 11/14* (2013.01); *A42B 1/068* (2013.01)

(58) Field of Classification Search
CPC ........... A42B 1/06; A42B 1/066; A42B 1/068; A42B 3/16; A61F 11/12; A61F 11/14; A45D 44/12; A63B 71/10; H04R 1/10; Y10T 24/44564
USPC ......................... 2/423, 209, 209.13; 132/277
See application file for complete search history.

(56) References Cited

U.S. PATENT DOCUMENTS

| | | | | |
|---|---|---|---|---|
| 280,005 A * | 6/1883 | Beard | ............... | A42B 1/068 2/172 |
| 379,965 A * | 3/1888 | Lippincott | .......... | A42B 1/066 2/172 |
| 782,769 A * | 2/1905 | Wallach | ............ | A42B 1/066 2/172 |
| 869,401 A * | 10/1907 | Callahan | ............ | A42B 1/066 132/59 |
| 1,438,171 A * | 12/1922 | Delson | ............... | A42B 1/068 2/172 |
| 2,333,392 A * | 11/1943 | Rosenzweig | ........ | A42B 1/068 2/195.5 |
| 4,850,055 A * | 7/1989 | Hwang | ................ | A61F 11/06 2/209 |
| D331,130 S * | 11/1992 | Williams | ............ | D29/112 |
| 5,426,790 A * | 6/1995 | Robertson | .......... | A42B 1/068 2/209 |
| 5,975,092 A * | 11/1999 | Tsai | ..................... | A45D 8/20 132/273 |
| 6,038,329 A * | 3/2000 | Lee | ...................... | H04R 1/105 379/430 |
| 6,357,642 B1 * | 3/2002 | Marchessault | ........ | A42B 1/24 2/209.13 |
| 2005/0028250 A1 * | 2/2005 | Zaic | ..................... | A42B 3/16 2/209 |
| 2006/0272135 A1 * | 12/2006 | Alitowski | ............ | A44B 99/00 24/507 |
| 2008/0257371 A1 * | 10/2008 | Silva | ..................... | A45D 8/20 132/210 |

* cited by examiner

*Primary Examiner* — Sally Haden
(74) *Attorney, Agent, or Firm* — Catherine Napjus; Michael Persson; Lawson, Persson & Chisholm, PC

(57) ABSTRACT

The present invention is an earmuff including first and second muff portions with a clip disposed between them. The clip is manipulatable into closed and open positions. When the clip is open, the upper sections of the first and second muff portions are separated. When the clip is closed, the upper sections are together. The earmuffs are designed to cover a human ear and are to be clipped to the headband of a cap by putting the earmuff into the open position, positioning the earmuff around the headband, and positioning the earmuff into the closed position.

20 Claims, 3 Drawing Sheets

CLIP-ON EARMUFF AND KIT

FIELD OF THE INVENTION

The present invention relates to cold weather accessories, and in particular, to earmuffs that are attachable to headwear.

BACKGROUND

Ears are particularly susceptible to the discomfort associated with cold weather. As such, throughout history, garments and accessories have been made to protect, cover, and/or warm ears. Such garments and accessories range from hats with ear flaps to balaclavas to headbands to earmuffs. Classic earmuffs include a band that stretches across one's head and end in a muff on each side that covers each ear. The band of the earmuff often includes an adjustment mechanism to accommodate larger or smaller heads. The band can be uncomfortable on the wearer's head and often slips around on the head so that the muff portion also slips from place on the ears. In addition, the attachment mechanism for the muffs to the band can be awkward and get caught in the wearer's hair. Therefore, there is a need for earmuffs that eschew the uncomfortable and unwieldy band and that stay in place over the wearer's ears.

Endeavors have been made toward this end. U.S. Pat. No. 379,965 to Lippincott, for example, discloses an earmuff with a fastening by which it is attached to the sweat-band of a hat. The fastening includes projections on one piece and corresponding depressions on the other piece, whereby the two pieces composing the attachment and being of spring metal may be locked together when positioned vertically to each other.

U.S. Pat. No. 2,303,850 to Liederman discloses a cap and earmuff combination where the cap has a cap band of stiffening material to which are riveted the means for attaching the earmuffs.

U.S. Pat. No. 2,333,392 to Rosenzweig discloses earmuffs which may be mounted on a hat or cap, where the earmuff includes a member made of a single piece of resilient wire that is external from the earmuff covering portion, a looped frame portion to support a covering, and a clamp consisting of a pair of pressed together spring clamp portions.

U.S. Pat. No. 2,442,825 to Rabushka discloses an earmuff arrangement for use upon a cap, which incorporates the use of bent metal clip-like members that preferably have depressed or indented portions therein.

U.S. Pat. No. 2,640,199 to Funk discloses a cap comprising a crown, a lining, and a headband disposed between the crown and the lining, said crown, lining and headband being secured together in the form of a unitary assembly and defining the lower edge of said cap, said crown being provided on each side above the region of the ears of the wearer when the cap is being worn with pairs of spaced parallel slits perpendicular to said edge, a relatively short strip of stiff material rigidly secured adjacent one of its ends to the headband on each side of the cap so as to be positioned above the ears of the wearer when the cap is being worn and passing outwardly through one of said slits and back inwardly through the other slit of each of said pairs so that a short portion of each of said strips is exposed, and swivel means swingably secured to the said exposed portions of each of said short strips for supporting earmuffs.

U.S. Pat. No. 3,050,739 to Fogarty discloses a device for supporting a pair of earmuffs that enables the support band to be retained on the head, while the earmuff support frame is slid along the band and clamped thereto in its adjusted position; the individual earmuff support frame being supported in such a manner that it can be rotated out of its normal mounting position, thereby moving the earmuffs away from the ears of the wearer.

U.S. Pat. No. 4,796,307 to Vantine discloses an ear protector for use with a headband or similar appliance, which protector comprises a cap member of sufficient size and shape for covering an ear; suspension means including first and second ends; means pivotally connecting the cap member to the first end of the suspension means for permitting the adjustable positioning of the cap member with respect to the disposition of the ear; means for attaching the second end of the suspension means to a headband; and means for securing the protector to the temple of an eyeglass frame, which securing means includes arms attached to the cap member, each arm having a free end, and means carried at each free end for detachably securing same to the temple.

U.S. Pat. No. 5,121,507 to Brown discloses an accessory attachment for headwear having a rearwardly disposed generally vertical rim portion extending around the rear portions of the headwear when applied to the head of a wearer, comprising, in combination, a plurality of U-shaped clips frictionally encompassing the rim portion and being positionable thereon in a plurality of selected peripherally spaced positions; each clip having a patch of hooked locking fibers secured to the outwardly facing surface of the clip; an accessory attachment formed of flexible material and having a band formed on its upper end; and a plurality of patched fibrous material secured to the band in the same spaced relationship as the clips, whereby the accessory attachment may be detachably secured to the locking fibers on the clips.

U.S. Pat. No. 5,426,790 to Robertson discloses an apparatus for protecting a person's ears from the damaging ultra-violet rays of the sun. The ear protector apparatus conveniently clips to the outside of a cap. The protective ear apparatus is positionable along the headband of the cap in accordance with the anatomical configuration of a person's head. Furthermore, the protective ear apparatus is removable and may be applied from one cap to another. The ear apparatus shades the ear, rather than covers it for warmth, like an earmuff.

U.S. Pat. No. 7,971,282 to Berge discloses earmuffs for use with protective headgear, primarily helmets, wherein the earmuffs are in the form of sleeves with flaps that overlap the edges of the sleeves, include a base element that spans a wearer's head and couples left and right sleeves, and include a chin cover that receives the portion of a chin strap that extends beyond the sleeve.

U.S. Patent App. No. 2008/0263749 to Leong discloses hearing protection muffs that comprise a sound attenuating cap, a self-attachment member for engaging the sound attenuating cap to the ear of a use, and optionally a sealing member.

U.S. Patent App. No. 2011/0113537 to Young-Hua Peng discloses a multifunction safety mask with earmuffs clip, composed of a front hoop ring equipped with a connection portion, including a brim hinge joint part, back hoop ring hinge joint part, and top belt hinge joint hole, wherein an earmuffs clamp groove is placed at the top side of the connection portion; a brim body hinged on the brim hinge joint part of the front hoop ring; a back hoop ring, in which the two ends of the back hoop ring are buckled in a front hoop ring and back hoop ring pivot hole; a top belt buckled, in which the two ends of the top belt are buckled in the top belt hinge joint hole placed at the two sides of the front hoop ring; and earmuffs including two earmuff bodies with a link plate between them, in which the two sides of the link plate enter and buckle in the earmuffs clamp groove; thus the mask not only is stably worn on a user's head, but also prevents the user from noise damage with the earmuffs stably buckled on the mask.

Although each of the above cited patents and patent application addresses some of the issues inherent in earmuffs none do so sufficiently. In particular, none is easily removable and reattachable and those that are removable either require a special attachment to the hat upon which they are attached or cause damage to the hat by virtue of their attachment mechanism, none may be easily and inexpensively manufactured, and none have a thin profile that allow them to easily fit in a wearer's pocket while not in use.

SUMMARY OF THE INVENTION

The present invention is a clip-on earmuff and a clip-on earmuff kit.

In its most basic form, the earmuff of the present invention includes a first muff portion with a first muff inside, a first muff outside, a first muff lower section, a first muff upper section, and a first muff central section; a second muff portion with a second muff inside, a second muff outside, a second muff lower section, a second muff upper section, and a second muff central section; and a clip between the first muff inside and the second muff inside. The first muff lower section and the second muff lower section are affixed to one another so that the first muff inside and the second muff inside face one another. The first muff upper section and the second muff upper section are not affixed. The first and second muff portions are of the same size and shape, which is at least 2 inches by 2 inches. The clip includes a first clip side disposed proximate to the first muff inside; a second clip side disposed proximate to the second muff inside; a closed end where the first clip side and the second clip side are affixed to one another; and an open end. The closed end is disposed between the first muff central section and the second muff central section. The open end includes a first open end side affixed to the first muff upper section and comprised by the first clip side, and a second open end side affixed to the second muff upper section and comprised by the second clip side. The clip is manipulatable between an open position where the first open end side and the second open end side are separated and a closed position wherein the first open end side and the second open end side are securely together.

The preferred clips are hairpin-type clips, butterfly-type clips, or binder-type clips, but any clip as described above may be used successfully with the present invention. With each of these preferred clips, the clips will remain in the closed position unless pressure is exerted on the clip in some way to force the clip into the open position. Once that pressure is released, the clip returns to the closed position.

The earmuffs may include a logo or other decoration on their outsides. They may be made of any material, but are preferably made a soft material for comfort, as they are worn against the ears, and a warm material, as one of their objects is to warm the ears. The earmuff may include an inner portion between and attached to the first and second muff insides to cover the clip. In addition to the clip being affixed to the first and second upper sections at the first and second open end sides of the clip, the clip may also be affixed to the first and second muff insides at the first and second clip sides of the clip and/or to the first and second muff central sections at the closed end of the clip.

In its most basic form, the earmuff kit of the present invention includes two substantially identical earmuffs of the present invention, as described above, and a headwear with an unobstructed headband. In this context, "substantially identical" means that each of the earmuffs is the same shape and size and has the same type of clips within the earmuff. The earmuffs may look different on their outsides, however. For example, they may be different colors or have different logos. So long as they are the same shape and size, and have the same clips within, they are considered "substantially identical" for purposes of the present invention. In this context, a headwear with an "unobstructed headband" means a headwear, such as a baseball cap, that does not have a brim or other disruption on the headband where the headband passes over where the ear of the headwear wearer would be. To be clear, a baseball cap, for example, does typically have a brim, but the brim does not pass over the part of the headband of the cap that will be over the ear of someone wearing the cap, so it has an "unobstructed headband." A baseball cap, therefore, qualifies as a headwear of the kit of the present invention. A fedora, on the other hand, typically has a brim that passes all the way around the headband of the hat. Such that a fedora would therefore not qualify as a headwear of the kit of the present invention because it does not have an "unobstructed headband."

In practice, the earmuff of the present invention is clipped to the headband of the headwear at a place on the headband that is right above the ear of a wearer of the headwear. A user will feel the clip within the earmuff and manipulate it into the open position; position the first and second muff portions on either side of that spot on the headband; and then release the clip back into the closed position so that the headband is caught between the first and second muff portions and the earmuff is held in place on the headband so that the earmuff covers the wearer's ear.

Therefore, is an aspect of the invention to provide an earmuff that is easily removable from and reattachable to a user's hat.

It is a further aspect of the invention to provide an earmuff that does not require a special attachment to the hat upon which they are attached.

It is a further aspect of the invention to provide an earmuff that will not cause damage to the hat by virtue of their attachment mechanism.

It is a further aspect of the invention to provide an earmuff that may be easily and inexpensively manufactured.

It is a still further aspect of the invention to provide an earmuff that has a thin profile that allow them to easily fit in a wearer's pocket while not in use.

These aspects of the present invention are not meant to be exclusive and other features, aspects, and advantages of the present invention will be readily apparent to those of ordinary skill in the art when read in conjunction with the following description and accompanying drawings.

DETAILED DESCRIPTION

Figure 1A:
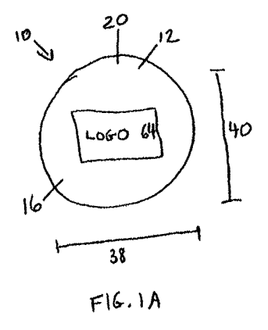
FIGS. 1A-1C are examples of different embodiments of the outside of the earmuff of the present invention.
Figure 1B:
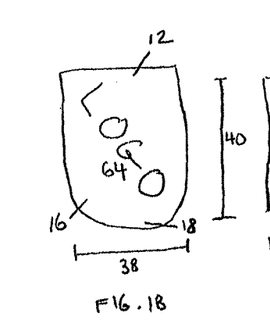
Figure 1C:
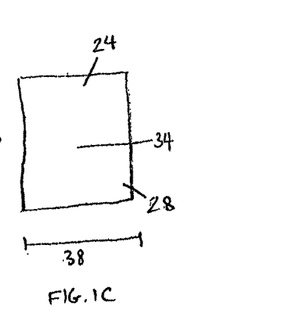

Referring first to FIGS. 1A-1C, examples of several embodiments of outside 16, 28 of earmuff 10 are provided. First muff portion 12 is indicated in FIGS. 1A and 1B. Second muff portion 24 is indicated in FIG. 1C. It is understood that the designation between first muff portion 12 and second muff portion 24 is arbitrary. First and second muff portions 12 and 24 are substantially identical and reversible in that they are of the same size and shape. First muff outside 16, second muff outside 28, first muff lower section 18, first muff upper section 20, and second muff central section 34 are also indicated. Earmuff 10 may be round, as shown in FIG. 1A. It may also be a rounded or rectangular flap, as shown in FIGS. 1B and 1C, respectively. The embodiments shown in FIGS. 1A-1C are merely exemplary, and one of at least ordinary skill in the art will recognize that the size and shape, both two-dimensionally and three-dimensionally, of an earmuff 10 of the present invention, may vary widely. The width 38 and height 40 of earmuff 10 must always be at least 2 inches for both dimensions, however, as the purpose of earmuff 10 is to cover and warm a human ear. If earmuff 10 were any smaller than 2"×2", it likely would not serve this purpose well. In requiring that the dimensions be at least 2"×2", it is not to suggest that earmuff 10 must be square. Instead, the requirement is that whatever shape earmuff 10 is, that shape have a width 38 of at least 2" and a length 40 of at least 2". Earmuff 10 may include a logo 64, which may be of any size on the outside 16 of earmuff 10. Logo 64 may be a word or design trademark, trade dress, or any other type of indicia. Logo 64 may be the mascot for a sports team, for example. Logo 64 may also simply be one or more of a sports team's colors. If a team's colors are maroon and blue, for example, logo 64 may be one earmuff 10 being maroon on the outside 16 or 28 and the other earmuff 10 being blue on the outside 16 or 28.

Figure 2A:
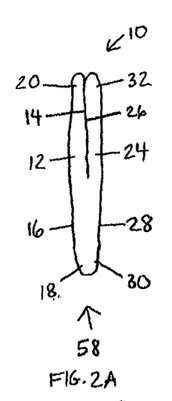
FIGS. 2A and 2B are side views of the earmuff of the present invention in closed and open positions, respectively.
Figure 2B:
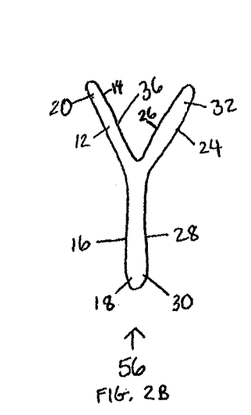
Figure 2C:
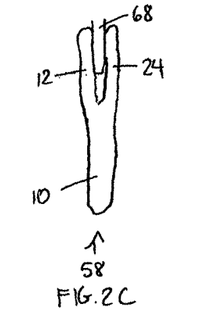
FIG. 2C is a side view of the earmuff of the present invention in the closed position and applied to a headband of a cap.

Now referring to FIGS. 2A-2C, side views of earmuff 10 in closed position 58, open position 56, and closed position 58 applied to a headband 68 are provided, respectively. Earmuff 10 includes first muff portion 12 and second muff portion 24. First muff portion 12 includes first muff inside 14, first muff outside 16, first muff lower section 18, and first muff upper section 20. Second muff portion 24 includes second muff inside 26, second muff outside 28, second muff lower section 30, and second muff upper section 32. First and second muff lower sections 18, 30 are affixed to one another so that first and second muff insides 14, 26 face one another. First and second muff lower sections 18, 30 may be affixed by any means commonly used in the art, such as by stitching, heat gluing, or other adhesion. First and second muff upper sections 20, 32 are not affixed to one another so that earmuff 10 may move between open position 56 and closed position 58. Although the separation between first and second muff sections 20, 32 is shown to extend about halfway down earmuff 10, it is understood that the separation may be smaller, so that the separation only extends a short distance down from first and second upper sections 20, 32, or larger so that the separation extends down further toward first and second lower sections 18, 30. The embodiment of earmuff 10 shown in FIGS. 2A-2C also includes inner portion 36, which covers clip 42, so that clip 42 is not visible even when earmuff 10 is in open position 56, as shown in FIG. 2B. This is as opposed to an embodiment such as that shown in FIG. 3B, discussed below, that does not include an inner portion 36, so that clip 42 is visible and uncovered, even when earmuff 10 is in open position 56. First clip side 44 includes first clip side inner side 45 and first clip side outer side 43. Second clip side 46 includes second clip side inner side 47 and second clip side outer side 49. As shown in FIG. 3B, first and second clip side inner sides 45, 47 are exposed when clip 42 is in open position 56, as opposed to first and second clip side inner sides 45, 47 in FIG. 2D, for example, which are covered by first and second muff portions 12, 24 even when clip 42 is in open position 56. In all embodiments, however, first and second clip side outer sides 43, 49 are completely covered by first and second muff portions 12, 24.

Figure 2D:
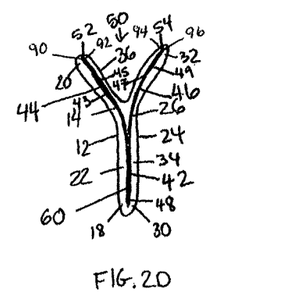
FIG. 2D is a cross-sectional view of the side view shown in FIG. 2B, showing the clip within the earmuff of the present invention.

Now referring to FIG. 2D, a cross-sectional view of the side view shown in FIG. 2B, showing clip 42 within earmuff 10 is provided. Clip 42 is a hairpin-type clip 60, which will be discussed in more detail with reference to FIGS. 3A and 3B. Clip 42 sits between first and second muff portions 12, 24, and is specifically set against first and second muff insides 14, 26. Clip 42 has first clip side 44, which is against first muff portion 12, and second clip side 46, which is against second muff portion 26. First and second clip sides 44, 46 come together at closed end 48 of clip 42. Closed end 42 is disposed between first and second muff central sections 22, 34. Central muff sections 22, 34 may be roughly in the middle of earmuff 10, or may extend higher toward upper sections 20, 32, or lower toward lower sections 18, 30, as shown in FIG. 2D. Clip 42 also includes open end 50, which includes first and second open end sides 52, 54 of clip 42. First open end side 52 includes first open end side outer side 90 and first open end side inner side 92. Second open end side 54 includes second open end side inner side 94 and second open end side outer side 96. First open end side outer side 90 is the tip of first clip side outer side 43; first open end side inner side 92 is the tip of first clip side inner side 45; second open end side inner side 94 is the tip of second clip side inner side 47; and second open end side outer side 96 is the tip of second clip side outer side 49. In some embodiments, such as that shown in FIG. 3B, first and second open end side inner sides 92, 94 may be exposed when clip 42 is in open position 56. In other embodiments, such as that shown in FIG. 2D, first and second open end inner sides 92, 94 may be covered by first and second muff portions 12, 24 when clip 42 is in open position 56. In either of the embodiments shown in FIGS. 2D and 3B, however, and, indeed, in all embodiments of clip 42, first and second open end side outer sides 90, 96 are covered by first and second muff portions 12, 24. Clip 42 is affixed to first and second muff portions 12, 24 in that the first and second open end sides 52, 54 are affixed to first and second upper sections 20, 32, respectively. This affixation may be made by heat gluing, epoxy, other adhesion, stitching, or any other affixation means commonly used in the art. It may also be removably affixed, as in embodiments of the kit of the present invention in which multiple muffs are provided.

Closed end 48 of clip 42 may also be similarly affixed to first and second muff central sections 22, 34. First and second clip sides 44, 46 may also be similarly affixed to first and second muff insides 14, 26. Earmuff 10 includes inner portion 36, which covers clip 42, so that clip 42 is not visible from the outside of earmuff 10, even when earmuff 10 is in open position 56. Inner portion 36 may be affixed to first and second muff insides 14, 26 by any means commonly used in the art, such as stitching or gluing.

Figure 3A:
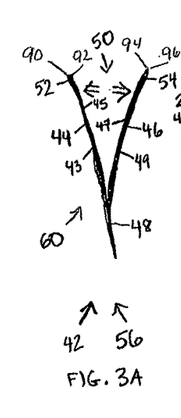
FIGS. 3A and 3B are side views of a hairpin-type clip alone and incorporated into an earmuff of the present invention, respectively.
Figure 3B:
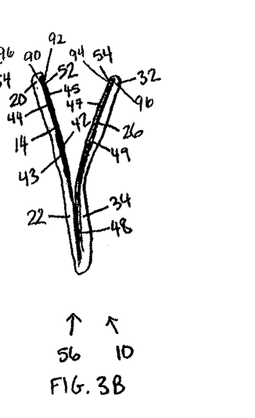

Now referring to FIGS. 3A and 3B, side views of hairpin-type clip 60 alone and incorporated into earmuff 10 are provided, respectively. Hairpin-type clip 60 is one preferred embodiment of clip 42. First and second clip sides 44, 46 of hairpin-type clip 60 are made of a flat, rigid material so that when first and second clip sides 44, 46 are placed against one another, they are flush with each other. First and second clip sides 44, 46 are held tightly together at closed end 50 by any means commonly used in the art, such as welding, bolting, etc. Hairpin-type clip 60 will therefore remain in closed position 56 unless pressure is applied to pull first and second clip sides 44, 46 apart into open position 56. Such pressure is indicated in FIG. 3A by arrows at open end 50. Once that pressure is released, hairpin-type clip 60 will naturally return to closed position 58. In FIG. 3B, inner portion 36 is not included, as it was in FIGS. 2B and 2D. First and second clip sides 44, 46 are therefore visible when earmuff 10 is in open position 56. First and second clip sides 44, 46 are set directly against first and second muff insides 14, 26. First and second open end sides 52, 54 of hairpin-type clip 60 are affixed to first and second muff upper sections 20, 32 as described above with reference to FIG. 2D. First and second clip sides 44, 46 may be affixed to first and second muff insides 14, 26 and closed end 48 may be affixed to first and second muff central sections 22, 34, also as described above with reference to FIG. 2D.

Figure 4A:
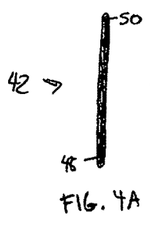
FIGS. 4A-4D are front views of various embodiments of clips that may be incorporated into an earmuff of the present invention.
Figure 4B:
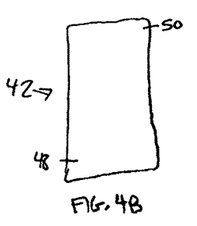
Figures 4C, 4D:
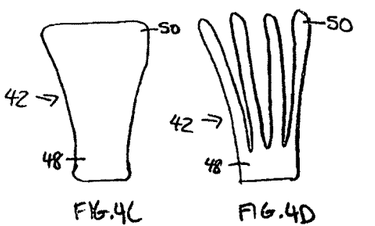

Now referring to FIGS. 4A-4D, front views of various embodiments of clips 42 that may be incorporated into earmuff 10 are provided. FIG. 4A shows a simple hairpin-type clip 60, as described in detail with reference to FIGS. 3A and 3B. Hairpin-type clip 60 may be sticklike as shown, but may also have a larger area as seen from the front, such as in FIG. 4B or 4C, while still being very straight and narrow from the side, as shown in FIGS. 3A and 3B. FIGS. 4B and 4C may be a hairpin-type clip 60, as discussed, but may also be a butterfly-type clip 62, as described in more detail with reference to FIGS. 5A-5C, or a binder-type clip 63, as described in more detail with reference to FIGS. 6A-6C. FIG. 4D is likely a butterfly-type clip 62. The side views of any clip 42 are going to be fairly thin and prong-like as shown in FIGS. 2D, 3A, 3B, 5A-5C, and 6A-6C. The front views of clip 42, on the other hand, may vary much more as far as area and shape. FIGS. 4A-4D illustrate just four examples of such variations. One of at least ordinary skill in the art will recognize that the fronts of clips 42 may be of many variations, and that the four shown in FIGS. 4A-4D do not limit such variations.

Figure 5A:
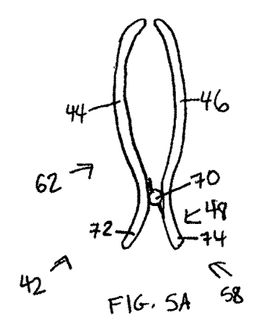
FIGS. 5A-5C are side views of a butterfly-type clip in a closed position, open position, and incorporated into an earmuff of the present invention, respectively.
Figure 5B:
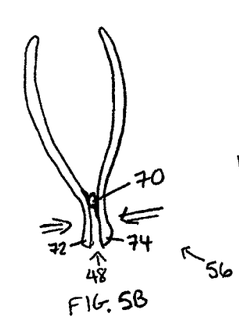
Figure 5C:
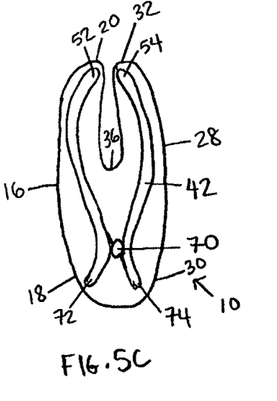

Now referring to FIGS. 5A-5C, side views of a butterfly-type clip 62 in closed position 58, open position 56, and incorporated into earmuff 10 are provided, respectively. Butterfly-type clip 62 is one preferred embodiment of clip 42. Butterfly-type clip 62 includes spring 70 at closed end 48 and first and second closed end sides 72, 74 extending down from spring 70 so that some portion of first and second clip sides 44, 46 are on either side of spring 70. Spring 70 is preferably a coil-type spring where one end of the spring extends slightly up first clip side 44 toward open end 50 and the other end of the spring extends slightly down second clip side 46 toward closed end 48, so that butterfly-type clip 62 will naturally tend to remain in closed position 58, as shown in FIG. 5A. If pressure, indicated by arrows in FIG. 5B, is applied to push first and second closed end sides 72, 74 together below spring 70, this will force first and second open end sides 52, 54 apart so that butterfly-type clip 62 is forced into open position 56, as shown in FIG. 5B. Once that pressure is released, butterfly-type clip 62 will return to closed position 58. Although first and second clip sides 44, 46 are shown as curved, it is understood that they may be substantially straight, so long as first and second closed end sides 72, 74 are curved or angled away from one another below spring 70 so that pressure may be exerted on them to push them together and have them spring back apart, as described. In FIG. 5C, we see butterfly-type clip 62 incorporated into earmuff 10. In this embodiment, earmuff 10 has slightly rounded first and second muff outsides 16, 28 to accommodate the curvature of first and second clip sides 44, 46. Other embodiments incorporating hairpin-type clips 60 or flatter butterfly-type clips 62 may have flatter first and second muff outsides 16, 28.

Figure 6A:
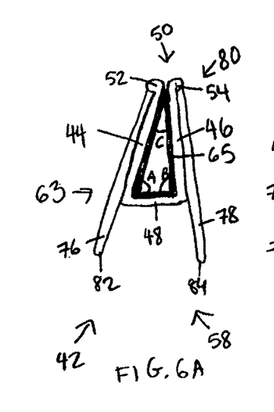
FIGS. 6A-6C are side views of a binder-type clip in a closed position, open position, and incorporated into an earmuff of the present invention, respectively.
Figure 6B:
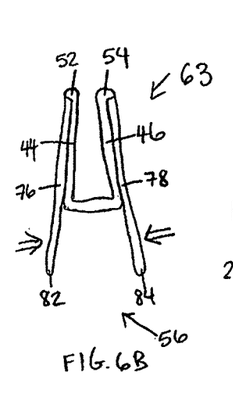
Figure 6C:
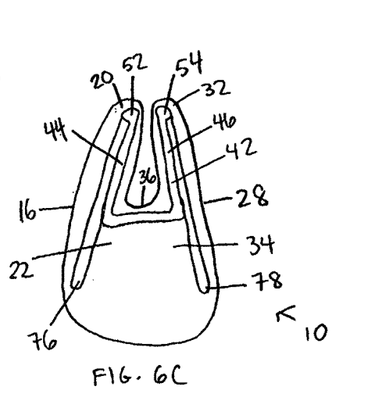

Now referring to FIGS. 6A-6C, side views of binder-type clip 63 in closed position 58, open position 56, and incorporated into earmuff 10 are provided, respectively. Binder-type clip 63 is one preferred embodiment of clip 42. Binder-type clip 63 is similar to a binder clip. Closed end 48 of binder-type clip 63 is flat. First and second clip sides 44, 46 extend upward on either side from closed end 48. When binder-type clip 63 is in closed position 58, as shown in FIG. 6A, emboldened cross-section 65 is substantially triangular, forming angle A between closed end 48 and first clip side 44; angle B between closed end 48 and second clip side 46; and angle C between first and second clip sides 44, 46. Binder-type clip 63 includes first and second clip levers 76, 78, which are affixed to first and second open end sides 52, 54 and extend flush along and beyond first and second clip sides 44, 46, ending in first and second lever ends 82, 84, so that first and second lever ends 82, 84 are beyond and lower than closed end 48. First and second clip levers 76, 78 are preferably affixed to first and second open end sides 52, 54 like a binder clip, with metal of first and second open end sides 52, 54 wrapped around the metal of the first and second clip levers 76, 78, but may be affixed by any means commonly used in the art, such as welding or bolting. Binder-type clip 63 will remain in closed position 58, as shown in FIG. 6A, unless pressure (indicated by arrows in FIG. 6B) is exerted to push first and second clip lever ends 84 toward one another, which forces first and second open end sides 52, 54 apart into open position 56, as shown in FIG. 6B. In FIG. 6C, we see binder-type clip 63 incorporated into earmuff 10. In this embodiment, earmuff 10 has rounded first and second muff outsides 16, 28 to accommodate the distance between first and second clip lever ends 82, 84.

Hairpin-type clip 60, shown in FIGS. 2D, 3A, and 3B; butterfly-type clip 62, shown in FIGS. 5A-5C; and binder-type clip 63, shown in FIGS. 6A-6C are preferred embodiments of clip 42. These embodiments should not be construed as limiting the embodiments considered to be a part of this invention. One of at least ordinary skill in the art will recognize that many types of clip 42 may be used successfully, as envisioned and described herein, when incorporated into earmuff 10 of the present invention.

Figure 7:
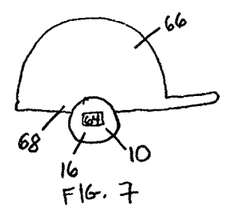
FIG. 7 is a side view of an earmuff of the present invention clipped to the headband of a cap.

Now referring to FIG. 7, a side view of earmuff 10 clipped to headband 68 of cap 66 is provided. Earmuff 10 will work most successfully with headwear 66 that does not include a brim that goes all the way around the head. Baseball caps, skull caps, wool caps, berets, etc. are examples of such headwear 66. It is difficult to used earmuff 10 with headwear, such as a fedora, that has a brim that encircles the headband 68 because earmuff 10 is clipped to the headband 68 of headwear 66 above the wearer's ear. Headband 68 of headwear 66 is the band or portion of headwear 66 that encircles the head of the wearer above the ear.

Although the present invention has been described in considerable detail with reference to certain preferred versions thereof, other versions would be readily apparent to those of ordinary skill in the art. Therefore, the spirit and scope of the description should not be limited to the description of the preferred versions contained herein.

What is claimed is:

1. An earmuff comprising:
    a first muff portion comprising a first muff inside, a first muff outside, a first muff lower section, a first muff upper section, and a first muff central section;
    a second muff portion comprising a second muff inside, a second muff outside, a second muff lower section, a second muff upper section, and a second muff central section, wherein:
        said first muff lower section and said second muff lower section are affixed to one another such that said first muff inside and said second muff inside face one another;
        said first muff upper section and said second muff upper section are not affixed;
        said first and second muff portions comprise a same size and shape, wherein said size is at least 2 inches by 2 inches; and
    a clip disposed between said first muff inside and said second muff inside, wherein said clip comprises:
        a first clip side disposed proximate to said first muff inside, wherein said first clip side comprises a first clip side inner side and a first clip side outer side;
        a second clip side disposed proximate to said second muff inside, wherein said second clip side comprises a second clip side inner side and second clip side outer side;
        a closed end where said first clip side and said second clip side are affixed to one another, wherein said closed end is disposed between said first muff central section and said second muff central section; and
        an open end comprising:
            a first open end side affixed to said first muff upper section, wherein said first clip side comprises said first open end side, and wherein said first open end side comprises a first open end side inner side and a first open end side outer side; and
            a second open end side affixed to said second muff upper section, wherein said second clip side comprises said second open end side, and wherein said second open end side comprises a second open end side inner side and a second open end side outer side;
        wherein said clip is manipulatable between an open position wherein said first open end side and said second open end side are separated and a closed position wherein said first open end side and said second open end side are securely together; and
        wherein said first muff portion and said second muff portion completely cover said clip.

2. The earmuff as claimed in claim 1, wherein said clip is a hairpin-type clip and maintains said closed position unless a pressure is applied to pry apart said first and second open end sides into said open position, and said clip will return to said closed position when the pressure is released.

3. The earmuff as claimed in claim 1, wherein said clip is a butterfly-type clip and said closed end further comprises a first closed end side, a second closed end side, and a spring, wherein said clip maintains said closed position unless a pressure is applied to push said first and second closed end sides together to engage said spring such that said clip moves into said open position, and said clip will return to said closed position when the pressure is released.

4. The earmuff as claimed in claim 1, wherein:
    said clip is a binder-type clip;
    said closed end of said clip is flat and said first and second clip sides extend upward from either side of said flat closed end, such that when said clip is in said closed position, a cross-section of said clip is triangular with angles where said flat closed end meets said first and second clip sides and where said first and second clip sides meet;
    said clip further comprises a first clip lever affixed to said first open end side and extending flush along said first clip side and beyond said closed end of said clip to a first clip lever end;
    said clip further comprises a second clip lever affixed to said second open end side and extending flush along said second clip side and beyond said closed end of said clip to a second clip lever end;
    said clip maintains said closed position unless a pressure is applied to push said first and second clip lever ends together such that said clip is forced into said open position and said clip will return to said closed position when the pressure is released.

5. The earmuff as claimed in claim 1, wherein at least one logo is affixed to at least one of said first muff outside and said second muff outside.

6. The earmuff as claimed in claim 1, further comprising an inner portion disposed between and attached to said first muff inside and said second muff inside, such that said inner portion is also disposed between said first clip side and said second clip side of said clip and such that said inner portion covers said clip such that said clip is not visible from an outside of said earmuff.

7. The earmuff as claimed in claim 1, wherein said closed end of said clip is affixed to said first and second muff central sections, between which said closed end is disposed.

8. The earmuff as claimed in claim 1, wherein said first and second clip sides of said clip are affixed to said first and second muff insides.

9. The earmuff as claimed in claim 1, wherein said first muff portion completely covers both said first clip side outer side and said first clip side inner side and said second muff portion completely covers both said second clip side outer side and said second clip side inner side.

10. An earmuff kit comprising:
    two substantially identical earmuffs, each of which comprises:
        a first muff portion comprising a first muff inside, a first muff outside, a first muff lower section, a first muff upper section, and a first muff central section;
        a second muff portion comprising a second muff inside, a second muff outside, a second muff lower section, a second muff upper section, and a second muff central section, wherein:
            said first muff lower section and said second muff lower section are affixed to one another such that said first muff inside and said second muff inside face one another;

said first muff upper section and said second muff upper section are not affixed; and
said first and second muff portions comprise a same size and shape, wherein said size is at least 2 inches by 2 inches; and
a clip disposed between said first muff inside and said second muff inside, wherein said clip comprises:
a first clip side disposed proximate to said first muff inside, wherein said first clip side comprises a first clip side inner side and a first clip side outer side;
a second clip side disposed proximate to said second muff inside, wherein said second clip side comprises a second clip side inner side and second clip side outer side;
a closed end where said first clip side and said second clip side are affixed to one another, wherein said closed end is disposed between said first muff central section and said second muff central section; and
an open end comprising:
a first open end side affixed to said first muff upper section, wherein said first clip side comprises said first open end side, and wherein said first open end side comprises a first open end side inner side and a first open end side outer side; and
a second open end side affixed to said second muff upper section, wherein said second clip side comprises said second open end side, and wherein said second open end side comprises a second open end side inner side and a second open end side outer side;
wherein said clip is manipulatable between an open position wherein said first open end side and said second open end side are separated and a closed position wherein said first open end side and said second open end side are securely together; and
wherein said first muff portion and said second muff portion completely cover said clip; and
a headwear comprising an unobstructed headband.

11. The earmuff kit as claimed in claim 10, wherein said clip is a hairpin-type clip and maintains said closed position unless a pressure is applied to pry apart said first and second open end sides into said open position, and said clip will return to said closed position when the pressure is released.

12. The earmuff kit as claimed in claim 10, wherein said clip is a butterfly-type clip and said closed end further comprises a first closed end side, a second closed end side, and a spring, wherein said clip maintains said closed position unless a pressure is applied to push said first and second closed end sides together to engage said spring such that said clip moves into said open position, and said clip will return to said closed position when the pressure is released.

13. The earmuff kit as claimed in claim 10, wherein:
said clip is a binder-type clip;
said closed end of said clip is flat and said first and second clip sides extend upward from either side of said flat closed end, such that when said clip is in said closed position, a cross-section of said clip is triangular with angles where said flat closed end meets said first and second clip sides and where said first and second clip sides meet;
said clip further comprises a first clip lever affixed to said first open end side and extending flush along said first clip side and beyond said closed end of said clip to a first clip lever end;
said clip further comprises a second clip lever affixed to said second open end side and extending flush along said second clip side and beyond said closed end of said clip to a second clip lever end;
said clip maintains said closed position unless a pressure is applied to push said first and second clip lever ends together such that said clip is forced into said open position and said clip will return to said closed position when the pressure is released.

14. The earmuff kit as claimed in claim 10, wherein at least one logo is affixed to at least one of said first muff outside and said second muff outside.

15. The earmuff kit as claimed in claim 10, further comprising an inner portion disposed between and attached to said first muff inside and said second muff inside, such that said inner portion is also disposed between said first clip side and said second clip side of said clip and such that said inner portion covers said clip such that said clip is not visible from an outside of said earmuff.

16. The earmuff kit as claimed in claim 10, wherein said closed end of said clip is affixed to and disposed between said first and second muff central sections.

17. The earmuff kit as claimed in claim 10, wherein said first clip sides of said clip is affixed to said first muff insides and said second clip side of said clip is affixed to said second muff inside.

18. The earmuff kit as claimed in claim 10, wherein said first muff portion completely covers both said first clip side outer side and said first clip side inner side and said second muff portion completely covers both said second clip side outer side and said second clip side inner side.

19. An earmuff kit for forming an earmuff comprising:
at least two muffs, each muff comprising
a first muff portion comprising a first muff inside, a first muff outside, a first muff lower section, a first muff upper section, and a first muff central section;
a second muff portion comprising a second muff inside, a second muff outside, a second muff lower section, a second muff upper section, and a second muff central section, wherein:
said first muff lower section and said second muff lower section are affixed to one another such that said first muff inside and said second muff inside face one another;
said first muff upper section and said second muff upper section are not affixed;
said first and second muff portions comprise a same size and shape, wherein said size is at least 2 inches by 2 inches; and
a clip dimensioned to be disposed between said first muff inside and said second muff inside, wherein said clip comprises:
a first clip side disposed proximate to said first muff inside, wherein said first clip side comprises a first clip side inner side and a first clip side outer side;
a second clip side disposed proximate to said second muff inside, wherein said second clip side comprises a second clip side inner side and second clip side outer side;
a closed end where said first clip side and said second clip side are affixed to one another, wherein said closed end is disposed between said first muff central section and said second muff central section; and
an open end comprising:
a first open end side affixed to said first muff upper section, wherein said first clip side comprises said first open end side, and wherein said first open end side comprises a first open end side inner side and a first open end side outer side; and a second open end side affixed to said second muff upper section, wherein said second clip side comprises said second open end side, and wherein said second open end side comprises a second open end side inner side and a second open end side outer side;

wherein said clip is manipulatable between an open position wherein said first open end side and said second open end side are separated and a closed position wherein said first open end side and said second open end side are securely together; and wherein said first muff portion and said second muff portion completely cover said clip.

20. The earmuff kit as claimed in claim 19, wherein said first muff portion completely covers both said first clip side outer side and said first clip side inner side and said second muff portion completely covers both said second clip side outer side and said second clip side inner side.

* * * * *